252-98 AU 166 EX
11/17/81 OR 4,301,021

United States Patent [19] [11] 4,301,021
Breant [45] Nov. 17, 1981

[54] N,N-DIETHYL-2-ETHYLHEXANAMIDE FRAGRANCES

[75] Inventor: Claude Bréant, Villeurbanne, France
[73] Assignee: Rhone-Poulenc Industries, Paris, France

[21] Appl. No.: 136,545
[22] Filed: Apr. 2, 1980
[30] Foreign Application Priority Data
Apr. 2, 1979 [FR] France ................................ 79 08693
[51] Int. Cl.[3] .......................... A61K 7/46; C11B 9/00; C11D 3/32; C11D 3/50
[52] U.S. Cl. ...................................... 252/98; 252/102; 252/117; 252/174.11; 252/522 R; 252/522 A; 252/544; 424/65; 424/73; 424/358; 564/215
[58] Field of Search .................... 252/174.11, 522, 102, 252/117, 544, 98; 260/561 R; 424/358, 65, 73

[56] References Cited
U.S. PATENT DOCUMENTS

| | | | |
|---|---|---|---|
| 3,644,653 | 2/1972 | Tcheiltcheff | 252/522 R |
| 3,909,462 | 9/1975 | Gubler | 252/522 R |
| 4,070,496 | 1/1978 | Rowsell et al. | 252/522 R |

*Primary Examiner*—Dennis L. Albrecht
*Attorney, Agent, or Firm*—Burns, Doane, Swecker & Mathis

[57] ABSTRACT

Perfumed compositions include, as an odorant therefor, an olfactory affecting amount of N,N-diethyl-2-ethylhexanamide.

16 Claims, No Drawings

N,N-DIETHYL-2-ETHYLHEXANAMIDE FRAGRANCES

BACKGROUND OF THE INVENTION

1. Field of the Invention

The present invention relates to novel perfume compositions, including novel perfume bases, and, more especially, to such perfume compositions comprised of the odorant, N,N-diethyl-2-ethylhexanamide.

2. Description of the Prior Art

The use of certain alkanoic acid amides for incorporation into perfume or insect repellent compositions has already been proposed to this art, but not one of such amides is either distinguished or characterized by any unique or original fragrance evoking a pleasant olfactory response. Thus, Einhorn et al, *Ber.*, 39, 1,223 (1906) report that N,N-diethyl-2-ethylbutanamide evolves a faint scent akin to that of menthol; French Pat. No. 1,572,332 notes that N,N-diethyldimethylpropanamide has a peppermint fragrance, while N,N-dimethyl-2-ethylbutanamide emits the fragrance of natural mint. In U.S. Pat. No. 3,909,462 there is attributed to N-phenyl-N-methyl-2-ethylbutanamide the odor of grapefruit, utilized in the formulation of food and herb aromas to develop a composition suitable for use as a base in perfumes having a lavender fragrance. Finally, A. S. Lutta et al, *Entomol. Obozrenie,* 45, 317–25 (1966) noted in a study of the insect repellent properties of the alkanamides, the agreeable odor of N,N-diethyloctamide, without reflecting upon any specific fragrance. It has since been determined that this particular amide has a weakly spicy odor that is relatively common. It too has been definitely ascertained that the amides of the $C_5$–$C_6$ alkanoic acids, with the exception of N-phenyl-N-methyl-2-ethylbutanamide, emit the more or less common mint odors. Furthermore, for a given acid, the character of the fragrance varies in direct response to the nature of the substituents borne by the amido nitrogen atom, but without, however, the ultimate fragrance evolved being predictable; thus, N,N-dimethyl-2-ethylbutanamide emits the fresh scent of natural mint, far stronger than that of the N,N-diethyl homolog, the scent of which latter derivative, even though also being that of mint, being much weaker and more akin to that of peppermint. On the other hand, the molecular structure of the acid significantly affects the fragrance of the amide; thus, N,N-diethylcaprylamide evolves a scent considerably different from that of N,N-diethyl-2-ethylbutanamide. It logically follows, therefore, that it is difficult, if not impossible for those skilled in this art to reliably predict whether or not a given alkanamide will have a pleasing odor from an olfactory sensation point of view and, if so, just what that particular fragrance would be.

Accordingly, the perfume industry is continuously seeking novel odorants and fragrances which by virtue of their uniqueness, availability and strength of scent are well adapted for formulation into perfume compositions which are completely unique.

SUMMARY OF THE INVENTION

Accordingly, a major object of the present invention is the provision of a novel odorant, and perfume compositions/formulations comprised thereof, all of which are characterized by an originally unique fragrance.

Briefly, the present invention features novel perfume compositions/formulations, whether perfume bases or final perfume products, each of which is characterized in that, in addition to the typical perfume ingredients or components comprising same, such products contain an effective fragrant, or fragrance attentuating amount of the odorant, N,N-diethyl-2-ethylhexanamide.

DETAILED DESCRIPTION OF THE INVENTION

More particularly, the present invention features perfume compositions/formulations, and perfume bases and perfumed products, each of which is characterized by including, as the active ingredient odorant thereof, an effective olfactory affecting amount of N,N-diethyl-2-ethylhexanamide [DEH].

N,N-diethyl-2-ethylhexanamide, which has the structural formula:

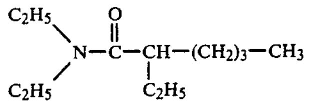

emits or gives off an original perfume fragrance combining the scents of a thorny rose, galbulus of eucalyptus having a slightly peppery jasmine fragrance. The powerful, diffusive and abundant nature of the subject odorant is atypically unique and, thus, such novel odorant is well adapted for per se use as a novel perfume, or for formulation into perfume compositions comprising DEH as either the sole odorant, or the DEH in combination with at least one other fragrance.

By the expression "perfume composition" or "formulation" any admixture of the different perfume ingredients, such as the typical solvents, solid or liquid perfume carriers, fixing agents, any one or more of the known fragrances or scents, and the like, and with which the N,N-diethyl-2-ethylhexanamide is formulated or incorporated, such admixtures being utilized to impart to any type of substrate, or finished or final product, the particular fragrance desired. The perfume bases constitute preferred examples of the perfume compositions consistent herewith wherein the N,N-diethyl-2-ethylhexanamide may be used to advantage. Other compositions wherein the DEH may advantageously be incorporated are the conventional detergent compositions. These compositions typically comprise one or more of the following ingredients: anionic, cationic or amphoteric surface active agents, bleaching agents, optical bluing or whitening agents, various fillers and anti-redeposition ingredients. The nature of these different ingredients is not critical and the N,N-diethyl-2-ethylhexanamide may be added to any type of detergent. Toilet waters, after shave lotions, perfumes, soaps and deodorant and sanitary products, for example in aerosol form, are exemplary of those substrates and final products which can be uniquely scented with N,N-diethyl-2-ethylhexanamide according to this invention.

N,N-diethyl-2-ethylhexanamide is itself a colorless liquid, boiling a 87° C. under a pressure of 1.5 mm Hg, and is very soluble in the conventional organic solvents, such as the alcohols, ketones, esters or ethers.

The amount of DEH in the various compositions according to the invention, expressed in percentages by weight in the particular composition under consideration, strictly depends on the nature of each such composition (perfume or toilet base, for example) and the intensity of the fragrance desired in the final product. It is thus obvious that in a perfume base the amount of N,N-diethyl-2-ethylhexanamide may be very high, for example, higher than 50% by weight, and as much as 90% by weight, while in a perfume, a toilet water, an after shave lotion or a soap, such amount may be considerably lower than 50% by weight. Thus, for all practical purposes the lower limit on the amount of N,N-diethyl-2-ethylhexanamide is that amount which effects a perceptible modification in the odor, fragrance, or scent of the final product. In certain cases, this minimum amount may be on the order of 0.01% by weight. Obviously, contents without the aforenoted range too may be utilized without departing from the scope of the present invention.

Moreover, the DEH incorporated per the invention is itself conveniently prepared by simply reacting a 2-ethylhexanoyl halide with diethylamine in the presence of an aqueous solution of an alkali metal base (preferably sodium or potassium).

In order to further illustrate the present invention and the advantage thereof. The following specific examples are given, it being understood that same are intended only as illustrative and in nowise limitative.

EXAMPLE 1

A perfume base having a floral scent was formulated from the following ingredients:

| | | |
|---|---|---|
| (i) | α-Hexylcinnamaldehyde; | 20 g |
| (ii) | Benzyl acetate; | 5 g |
| (iii) | 4-Nonanolide; | 0.5 g |
| (iv) | Pure rose oil; | 10 g |
| (v) | Tonquin musk, 3% by weight in ethanol; and | 2 g |
| (vi) | N,N-Diethyl-2-ethylhexanamide [DEH] | 62.5 g |

The DEH inparted to this floral fragrence the fine flowery scent of rose by aiding in the emitting of the volatile pure rose oil and by imbuing the jasmine scent with a strikingly natural aroma.

EXAMPLE 2

A peppermint base was formulated from the following ingredients:

| | | |
|---|---|---|
| (i) | Eugenol; | 10 g |
| (ii) | Isoeugenol; | 10 g |
| (iii) | Methyl dihydrojasmonate; | 5 g |
| (iv) | Essential oil of black pepper; | 5 g |
| (v) | Isobornylcyclohexanol; and | 10 g |
| (vi) | DEH | 60 g |

In the foregoing composition, the DEH enhanced the apparent concentration of the pepper scent and added thereto a scent of galbulus of eucalyptus and of pepperly rosebud.

EXAMPLE 3

A lilac base was formulated from the following ingredients:

| | | |
|---|---|---|
| (i) | Terpineol; | 20 g |
| (ii) | Linalol; | 5 g |
| (iii) | Benzyl acetate; | 10 g |
| (iv) | Linalyl acetate; | 5 g |
| (v) | β-Phenylethyl alcohol; | 10 g |
| (vi) | 60 -Hexylcinnamaldehyde; | 5 g |
| (vii) | Essential oil of Styrax; | 10 g |
| (viii) | Anisaldehyde diethyl acetal; and | 10 g |

-continued

| | | |
|---|---|---|
| (ix) | DEH | 25 g |

The DEH imparted to this formulation an exceptional lilac bouquet combined with the natural freshness of its floral scent, the strong and penetrating scent of eucalyptus, and the rosy scent of lilac.

EXAMPLE 4

150 g of N,N-diethyl-2-ethylhexanamide were added to a lemon based washing powder comprised of the following ingredients:

| | | |
|---|---|---|
| (i) | Essence of peel of mandarin orange; | 30 g |
| (ii) | Essence of grapefruit; | 50 g |
| (iii) | Essence of cypress; | 10 g |
| (iv) | Essence of Florida orange; | 120 g |
| (v) | Essence of lemon peel; | 80 g |
| (vi) | Essence of Java citronella; | 30 g |
| (vii) | d-Limonene; | 260 g |
| (viii) | Isobornylcyclohexanol | 50 g |
| (ix) | Para-tertbutylcyclohexyl acetate; | 10 g |
| (x) | Isocyclocitral | 5 g |
| (xi) | Citral; | 95 g |
| (xii) | diPhenyl oxide; | 30 g |
| (xiii) | Hexylcinnamaldehyde; | 35 g |
| (xiv) | $C_{10}$ aldehyde; and | 15 g |
| (xv) | Terpene oils of geranium | 30 g |
| | | 850 g |

The DEH formulation was then compared to the lemon scented base, per se, and it was determined that incorporation of the N,N-diethyl-2-ethylhexanamide attenuated the artificial nature of the base powder and imparted to the composition the natural scent of ripe lemon peels.

COMPARATIVE EXAMPLE A

In each of the compositions described in the foregoing Examples 1 to 3, the DEH was replaced with dipropylene glycol which functioned as a neutral solvent. In each case, such replacement resulted in the complete loss of those characteristics noted as being imparted upon the respective compositions by the DEH.

COMPARATIVE EXAMPLE B

In each of the compositions described in the foregoing Examples 1 to 3, the DEH was replaced by one of the following amides:

(i) N,N-diethyl-2-ethylbutanamide;
(ii) N,N-diethyl-2,2-dimethylpropanamide;
(iii) N,N-dimethyl-2-ethylbutanamide;
(iv) N-phenyl-N-methyl-2-ethylbutanamide; and
(v) N,N-diethylcaprylamide.

In each case, the fragrance imparted to the respective composition by DEH had totally disappeared, and the more common mint or camphor scents appeared in its stead.

The DEH utilized in the preceding examples was a colorless liquid, having a boiling point of 87° C. under a pressure of 1.5 mm Hg; its density at 20° C. was 0.869 and its index of refraction was 1.447. Such compound was prepared in the following manner:

Into a stainless steel reactor having a capacity of 3.81 and equipped with means for mechanical agitation, an internal thermometer, a 1 liter discharge ampoule and water cooling means, 892 g water were charged. The agitator was actuated and over the course of 40 minutes, 824 g diethylamine were added, while maintaining the temperature under 20° C. Subsequently, 824 g 2-ethylhexanoyl chloride were added thereto, over a period of 3 hours. The agitation was continued for 2 more hours at a temperature of less than 20° C., followed by the separation of the organic layer, which was washed, first with 300 ml of a 10% aqueous solution of sodium hydroxide, and then with 200 ml of a 5% by weight aqueous solution of sodium hydroxide. The organic layer was then distilled. A product was obtained, which was treated with active carbon under a nitrogen blanket. After filtration, 1,033 g of a product having the aforenoted characteristics was obtained, the elemental analysis and infra red spectrum thereof being that of a compound having the structural formula:

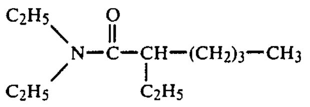

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a perfumed composition, the improvement which comprises, as an odorant therefor, an olfactory affecting amount of N,N-diethyl-2-ethylhexanamide (DEH).

2. The perfumed composition as defined by claim 1, the same comprising at least one other fragrance in addition to said DEH.

3. The perfumed composition as defined by claims 1 or 2, the same comprising a perfume solvent.

4. The perfumed composition as defined by claims 1 or 2, the same comprising a solid or liquid perfume carrier.

5. The perfumed composition as defined by claims 1 or 2, the same comprising a fixing agent.

6. The perfumed composition as defined by claim 1, comprising a detergent or soap.

7. The perfumed composition as defined by claim 1, comprising a toilet water.

8. The perfumed composition as defined by claim 1, comprising an after shave lotion.

9. The perfumed composition as defined by claim 1, comprising a deodorant.

10. The perfumed composition as defined by claim 1, comprising a liquid perfume.

11. The perfumed composition as defined by claim 6, further comprising at least one member selected from the group consisting of a surfactant, a bleaching agent, an optical bluing or whitening agent, a filler and an anti-redeposition agent.

12. The perfumed composition as defined by claim 1, comprising from 50% to 90% by weight of DEH.

13. The perfumed composition as defined by claim 1, comprising from 0.01% to 50% by weight of the DEH.

14. The method of perfuming a substrate, comprising applying thereto an olfactory affecting amount of N,N-diethyl-2-ethylhexanamide.

15. The method of perfuming a substrate, comprising applying thereto the perfumed composition as defined by claim 1.

16. The method as defined by claims 14 or 15, said substrate being human skin.

* * * * *